United States Patent
Gliner (10) Patent No.: US 12,004,862 B2
(45) Date of Patent: Jun. 11, 2024

(54) REMOVING FAR-FIELD FROM INTRACARDIAC SIGNALS

(71) Applicant: BIOSENSE WEBSTER (ISRAEL) LTD., Yokneam (IL)

(72) Inventor: Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 478 days.

(21) Appl. No.: 17/352,747

(22) Filed: Jun. 21, 2021

(65) Prior Publication Data
US 2022/0061730 A1 Mar. 3, 2022

Related U.S. Application Data

(60) Provisional application No. 63/073,414, filed on Sep. 1, 2020, provisional application No. 63/070,897, filed on Aug. 27, 2020.

(51) Int. Cl.
*A61B 5/318* (2021.01)
*A61B 5/00* (2006.01)
(Continued)

(52) U.S. Cl.
CPC .............. *A61B 5/346* (2021.01); *A61B 5/343* (2021.01); *A61B 5/6852* (2013.01); *G06N 3/04* (2013.01);
(Continued)

(58) Field of Classification Search
CPC ....... A61B 5/346; A61B 5/343; A61B 5/6852; G16H 40/67; G16H 15/00; G16H 50/20; G06N 3/04; G06N 3/08
See application file for complete search history.

(56) References Cited

U.S. PATENT DOCUMENTS 5,391,199 A  2/1995  Ben Haim
6,064,905 A  5/2000  Webster, Jr.
(Continued)

FOREIGN PATENT DOCUMENTS

CN  110974217 A  4/2020
WO  WO1996005768 A1  2/1996

OTHER PUBLICATIONS

Peng Xiong et al. "A stacked contractive denoising auto-encoder for ECG signal denoising." Physiological Measurement, vol. 37 Nov. 21, 2016, pp. 2214-2230 (Year: 2016).*

(Continued)

*Primary Examiner* — Eric D. Bertram (57) ABSTRACT

In one embodiment, a method includes receiving first intracardiac signals including first far-field components captured by at least one first sensing electrode of a first catheter, the at least one sensing electrode being in contact with tissue of a cardiac chamber of a first living subject, and at least one far-field signal captured from at least one far-field electrode inserted into the cardiac chamber and not in contact with the tissue of the cardiac chamber, training a neural network to remove far-field components from intracardiac signals responsively to the first intracardiac signals and the at least one far-field signal, receiving second intracardiac signals captured by at least one second sensing electrode of a second catheter inserted into a cardiac chamber of a second living subject, and applying the trained neural network to the second intracardiac signals to remove respective second far-field components from the second intracardiac signals.

18 Claims, 9 Drawing Sheets

(51) Int. Cl.
    *A61B 5/343*     (2021.01)
    *A61B 5/346*     (2021.01)
    *G06N 3/04*     (2023.01)
    *G06N 3/08*     (2023.01)
    *G16H 15/00*     (2018.01)
    *G16H 40/67*     (2018.01)
    *G16H 50/20*     (2018.01)

(52) U.S. Cl.
CPC ............... *G06N 3/08* (2013.01); *G16H 15/00* (2018.01); *G16H 40/67* (2018.01); *G16H 50/20* (2018.01)

(56) References Cited

U.S. PATENT DOCUMENTS

| | | | |
|---|---|---|---|
| 6,226,542 B1 | 5/2001 | Reisfeld | |
| 6,239,724 B1 | 5/2001 | Doron | |
| 6,301,496 B1 | 10/2001 | Reisfeld | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben Haim | |
| 6,814,733 B2 | 11/2004 | Schwartz | |
| 6,892,091 B1 | 5/2005 | Ben Haim | |
| 6,997,924 B2 | 2/2006 | Schwartz | |
| 7,156,816 B2 | 1/2007 | Schwartz | |
| 7,536,218 B2 | 5/2009 | Govari | |
| 7,756,576 B2 | 7/2010 | Levin | |
| 9,833,161 B2 * | 12/2017 | Govari | A61B 5/7203 |
| 10,045,707 B2 * | 8/2018 | Govari | A61B 5/6859 |
| 11,660,050 B2 * | 5/2023 | Govari | A61B 5/6853 600/374 |
| 2002/0065455 A1 | 5/2002 | Ben Haim | |
| 2003/0120150 A1 | 6/2003 | Govari | |
| 2004/0068178 A1 | 4/2004 | Govari | |
| 2014/0005664 A1 | 1/2014 | Govari | |
| 2017/0172442 A1 * | 6/2017 | Govari | A61B 5/287 |
| 2017/0202471 A1 | 7/2017 | Urman | |
| 2018/0296113 A1 | 10/2018 | Stewart | |
| 2019/0200886 A1 | 7/2019 | Welsh | |
| 2020/0129125 A1 * | 4/2020 | Govari | A61B 5/6858 |
| 2021/0378597 A1 * | 12/2021 | Amos | G06F 18/24143 |
| 2022/0061768 A1 * | 3/2022 | Gliner | A61B 5/7203 |

OTHER PUBLICATIONS

Lorenz, Nick Johannes, Unger, Laura Anna, Luik, Armin and Dössel, Olaf. "Quantitative assessment of ventricular far field removal techniques for clinical unipolar electrograms" Current Directions in Biomedical Engineering, vol. 7, No. 2, 2021, pp. 243-246. https://doi.org/10.1515/cdbme-2021-2062 (Year: 2021).*

Saha et al. "A Ventricular Far-field Artefact Filtering Technique for Atrial Electrograms." Computing in Cardiology, vol. 46, 2019, pp. 1-4 (Year: 2019).*

Frisch et al. "Mapping and Removing the Ventricular Far Field Component in Unipolar Atrial Electrograms." IEEE Transactions on Biomedical Engineering, vol. 67, No. 10, Oct. 2020, pp. 2905-2915. (Year: 2020).*

European Search Report for corresponding EPA No. 21193159.7 dated Feb. 2, 2022.

Xiong Peng et al., "ECG signal enhancement based on improved denioising auto-encoder", Engineering Applications of Artificial Intelligence, vol. 52, May 6, 2016.

* cited by examiner

REMOVING FAR-FIELD FROM INTRACARDIAC SIGNALS

RELATED APPLICATION INFORMATION

The present application claims the benefit of U.S. Provisional Patent Application No. 63/070,897, filed 27 Aug. 2020, and U.S. Provisional Patent Application No. 63/073,414, filed 1 Sep. 2020, the disclosures of which are hereby incorporated herein by reference.

FIELD OF THE INVENTION

The present invention relates to medical systems, and in particular, but not exclusively to, processing cardiac signals.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied between the catheter electrode(s) of the ablating catheter and an indifferent electrode (which may be one of the catheter electrodes), and current flows through the media between the electrodes, i.e., blood and tissue. The distribution of current may depend on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. In some applications, irreversible electroporation may be performed to ablate the tissue.

Electrode sensors in a cardiac chamber may detect far-field electrical activity, i.e., the ambient electrical activity originating away from the sensors, which can distort or obscure local electrical activity, i.e., signals originating at or near the sensors. Commonly assigned U.S. Patent Application Publication No. 2014/0005664 of Govari et al., discloses distinguishing a local component in an intracardiac electrode signal, due to the tissue with which the electrode is in contact from a remote-field contribution to the signal, and explains that a therapeutic procedure applied to the tissue can be controlled responsively to the distinguished local component.

SUMMARY

There is provided in accordance with an embodiment of the present disclosure, a method for analyzing signals, including receiving first intracardiac signals including first far-field components captured by at least one first sensing electrode of a first catheter, the at least one sensing electrode being in contact with tissue of a cardiac chamber of a first living subject, and at least one far-field signal captured from at least one far-field electrode inserted into the cardiac chamber and not in contact with the tissue of the cardiac chamber, training an artificial neural network to remove far-field components from intracardiac signals responsively to the received first intracardiac signals and the at least one far-field signal, receiving second intracardiac signals captured by at least one second sensing electrode of a second catheter inserted into a cardiac chamber of a second living subject, and applying the trained artificial neural network to the second intracardiac signals to remove respective second far-field components from the second intracardiac signals.

Further in accordance with an embodiment of the present disclosure, the method includes computing the first intracardiac signals with the respective first far-field components removed responsively to the at least one far-field signal, wherein the training includes training the artificial neural network responsively to the computed first intracardiac signals with the respective first far-field components removed.

Still further in accordance with an embodiment of the present disclosure the training includes training an autoencoder including an encoder and a decoder.

Additionally, in accordance with an embodiment of the present disclosure, the method includes rendering to a display a representation of at least one of the second intracardiac signals with a respective one of the second far-field components removed.

Moreover, in accordance with an embodiment of the present disclosure, the method includes generating and rendering to a display, an electroanatomic map responsively to at least one of the second intracardiac signals with a respective one of the second far-field components removed.

Further in accordance with an embodiment of the present disclosure the first catheter includes the at least one far-field electrode.

There is also provided in accordance with still another embodiment of the present disclosure a method for analyzing signals, including receiving intracardiac signals captured by at least one sensing electrode of a catheter inserted into a cardiac chamber of a living subject, and applying a trained artificial neural network to the intracardiac signals to remove respective far-field components from the intracardiac signals.

Still further in accordance with an embodiment of the present disclosure, the method includes rendering to a display a representation of at least one of the intracardiac signals with a respective one of the far-field components removed.

Additionally, in accordance with an embodiment of the present disclosure, the method includes generating and rendering to a display, an electroanatomic map responsively to at least one of the intracardiac signals with a respective one of the far-field components removed.

There is also provided in accordance with another embodiment of the present disclosure a software product, including a non-transient computer-readable medium in which program instructions are stored, which instructions, when read by a central processing unit (CPU), cause the CPU to receive first intracardiac signals including first far-field components captured by at least one first sensing electrode of a first catheter, the at least one sensing electrode being in contact with tissue of a cardiac chamber of a first living subject, and at least one far-field signal captured from at least one far-field electrode inserted into the cardiac chamber and not in contact with the tissue of the cardiac chamber, and train an artificial neural network to remove far-field components from intracardiac signals responsively to the received first intracardiac signals and the at least one far-field signal.

Further in accordance with an embodiment of the present disclosure, wherein the instructions, when read by the CPU, also cause the CPU to receive second intracardiac signals captured by at least one second sensing electrode of a second catheter inserted into a cardiac chamber of a second living subject, and apply the trained artificial neural network to the second intracardiac signals to remove respective second far-field components from the second intracardiac signals.

Still further in accordance with an embodiment of the present disclosure, wherein the instructions, when read by the CPU, also cause the CPU to compute the first intracardiac signals with the respective first far-field components removed responsively to the at least one far-field signal, and train the artificial neural network responsively to the computed first intracardiac signals with the respective first far-field components removed.

Additionally, in accordance with an embodiment of the present disclosure, wherein the instructions, when read by the CPU, also cause the CPU to render to a display a representation of at least one of the second intracardiac signals with a respective one of the second far-field components removed.

Moreover, in accordance with an embodiment of the present disclosure, wherein the instructions, when read by the CPU, also cause the CPU to generate and render to a display, an electroanatomic map responsively to at least one of the second intracardiac signals with a respective one of the second far-field components removed.

There is also provided in accordance with still another embodiment of the present disclosure a software product, including a non-transient computer-readable medium in which program instructions are stored, which instructions, when read by a central processing unit (CPU), cause the CPU to receive intracardiac signals captured by at least one sensing electrode of a catheter inserted into a cardiac chamber of a living subject, and apply a trained artificial neural network to the intracardiac signals to remove respective far-field components from the intracardiac signals.

Further in accordance with an embodiment of the present disclosure, wherein the instructions, when read by the CPU, also cause the CPU to render to a display a representation of at least one of the intracardiac signals with a respective one of the far-field components removed.

Still further in accordance with an embodiment of the present disclosure, wherein the instructions, when read by the CPU, also cause the CPU to generate and render to a display, an electroanatomic map responsively to at least one of the intracardiac signals with a respective one of the far-field components removed.

There is also provided in accordance with still another embodiment of the present disclosure a medical system, including a first catheter including at least one first sensing electrode configured to be inserted into a cardiac chamber of a first living subject, and a processor configured to receive first intracardiac signals including first far-field components captured by the at least one first sensing electrode of the first catheter, the at least one sensing electrode being in contact with tissue of the cardiac chamber of the first living subject, and at least one far-field signal captured from the at least one far-field electrode inserted into the cardiac chamber and not in contact with the tissue of the cardiac chamber, and train an artificial neural network to remove far-field components from intracardiac signals responsively to the received first intracardiac signals and the at least one far-field signal.

Moreover, in accordance with an embodiment of the present disclosure the processor is configured to compute the first intracardiac signals with the respective first far-field components removed responsively to the at least one far-field signal, and train the artificial neural network responsively to the computed first intracardiac signals with the respective first far-field components removed.

Further in accordance with an embodiment of the present disclosure the artificial neural network includes an autoencoder including an encoder and a decoder, the processor being configured to train the autoencoder to remove the far-field components from intracardiac signals responsively to the received first intracardiac signals and the at least one far-field signal.

Still further in accordance with an embodiment of the present disclosure, the system includes a second catheter including at least one second sensing electrode configured to be inserted into a cardiac chamber of a second living subject, wherein the processor is configured to receive second intracardiac signals captured by the at least one second sensing electrode of the second catheter inserted into the cardiac chamber of the second living subject, and apply the trained artificial neural network to the second intracardiac signals to remove respective second far-field components from the second intracardiac signals.

Additionally, in accordance with an embodiment of the present disclosure the trained artificial neural network includes an autoencoder including an encoder and a decoder, the processor being configured to apply the autoencoder to the second intracardiac signals to remove the respective second far-field components from the second intracardiac signals.

Moreover, in accordance with an embodiment of the present disclosure, the system includes a display, wherein the processor is configured to render to the display a representation of at least one of the second intracardiac signals with a respective one of the second far-field components removed.

Further in accordance with an embodiment of the present disclosure, the system includes a display, wherein the processor is configured to generate and render to the display, an electroanatomic map responsively to at least one of the second intracardiac signals with a respective one of the second far-field components removed.

Still further in accordance with an embodiment of the present disclosure the first catheter includes the at least one far-field electrode.

Additionally, in accordance with an embodiment of the present disclosure the first catheter includes an expandable distal end basket assembly, the at least one first sensing electrode being disposed on the basket assembly, the at least one far-field electrode being disposed in the basket assembly to prevent the at least one far-field electrode from contacting the tissue of the cardiac chamber of the first living subject.

There is also provided in accordance with still another embodiment of the present disclosure a medical system, including a catheter including at least one sensing electrode configured to be inserted into a cardiac chamber of a living subject, and a processor configured to receive intracardiac signals captured by the at least one sensing electrode inserted into the cardiac chamber, and apply a trained artificial neural network to the intracardiac signals to remove respective far-field components from the intracardiac signals.

Moreover, in accordance with an embodiment of the present disclosure the trained artificial neural network includes an autoencoder including an encoder and a decoder, the processor being configured to apply the autoencoder to the intracardiac signals to remove respective far-field components from the intracardiac signals.

Further in accordance with an embodiment of the present disclosure, the system includes a display, wherein the processor is configured to render to the display a representation of at least one of the intracardiac signals with a respective one of the far-field components removed.

Still further in accordance with an embodiment of the present disclosure, the system includes a display, wherein the processor is configured to generate and render to the display, an electroanatomic map responsively to at least one of the intracardiac signals with a respective one of the far-field components removed.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

As previously mentioned, electrode sensors in a cardiac chamber may detect far-field electrical activity, i.e., the ambient electrical activity originating away from the sensors, which can distort or obscure local electrical activity, i.e., signals originating at or near the sensors. Removal of far-field electrical activity from an intracardiac signal is not a trivial problem. This is because far-field appearance is dependent on many factors including electrode shape and size, location of the catheter, anatomy etc. Additionally, far-field and near-field share common frequencies and therefore simply using low-pass, high-pass, or band-pass filters does not provide a satisfactory solution.

Certain catheters may be used to provide signals which may be used to remove far-field components from intracardiac signals. For example, a basket catheter may include a central electrode, placed in the middle of the basket, which remains distant enough from cardiac tissue to provide a reasonable estimate of the far-field components. The signals sensed by the central electrode may be used to remove far-field components from intracardiac signals sensed by the basket electrodes. However, not all catheters have an electrode which only measures the far field. For example, balloon catheters or flat grid catheters do not include electrodes which are far enough away from tissue at all times. For such catheters, the problem of removing far-field components from the sensed intracardiac signals remains.

Embodiments of the present invention solve the above problems by training an artificial neural network (ANN), such as an autoencoder, to remove far-field components from intracardiac signals based on a set of training signals. The training signals may be provided by a basket catheter, which captures intracardiac signals in a cardiac chamber and also concurrently captures far-field signals using a far-field electrode (such as a central electrode disposed in the center of the basket assembly of the basket catheter).

The ANN may be trained by inputting the captured intracardiac signals into the ANN. Using an iterative process, parameters of the ANN are iteratively updated to reduce the difference between the actual output of the ANN and the desired output (e.g., the intracardiac signals with the far-field components removed).

Once trained, the ANN may be applied to other intracardiac signals captured by another catheter (e.g. a catheter without a "far-field electrode") in the same patient or a different patient to remove far-field components from the captured intracardiac signals.

In some embodiments, the weights of the ANN may be sent to a cloud server in which the ANN may execute to remove far-field components from intracardiac signals sent to the server.

System Description

Figure 1:
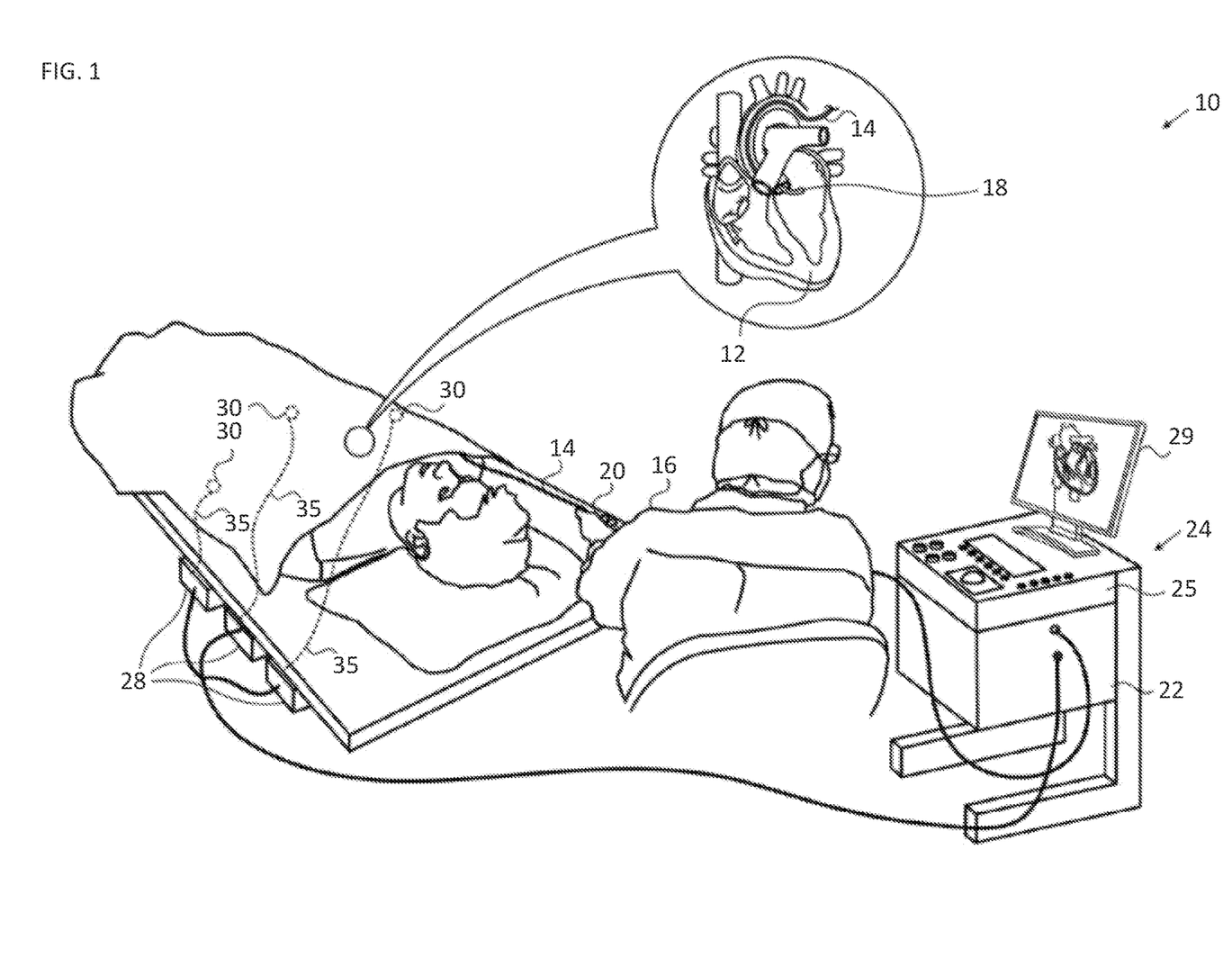
FIG. 1 is a pictorial illustration of a system for performing catheterization procedures on a heart, constructed and operative in accordance with an exemplary embodiment of the present invention.

Reference is now made to FIG. 1, which is a pictorial illustration of a medical system 10 for performing catheterization procedures on a heart 12, constructed and operative in accordance with an embodiment of the present invention. The medical system 10 may be configured to evaluate electrical activity and performing ablative procedures on the heart 12 of a living subject. The system comprises a catheter 14, which is percutaneously inserted by an operator 16 through the patient's vascular system into a chamber or vascular structure of the heart 12. The operator 16, who is typically a physician, brings the catheter's distal end 18 into contact with the heart wall, for example, at an ablation target site. Electrical activation maps may be prepared, according to the methods disclosed in U.S. Pat. Nos. 6,226,542, 6,301,496, and 6,892,091. One commercial product embodying elements of the system 10 is available as the CARTO® 3 System, available from Biosense Webster, Inc., 3333 Diamond Canyon Road, Diamond Bar, CA 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal end 18, which apply the radiofrequency energy to the myocardium. The energy is absorbed in the tissue, heating it to a point at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end 18 of the catheter 14 as desired for the ablation. To aid the operator 16, a distal portion of the catheter 14 contains position sensors (not shown) that provide signals to a processor 22, located in a console 24. The processor 22 may fulfill several processing functions as described below.

Wire connections 35 may link the console 24 with body surface electrodes 30 and other components of a positioning sub-system for measuring location and orientation coordinates of the catheter 14. The processor 22 or another processor (not shown) may be an element of the positioning subsystem. Catheter electrodes (not shown) and the body surface electrodes 30 may be used to measure tissue impedance at the ablation site as taught in U.S. Pat. No. 7,536,218. Temperature sensors (not shown), typically a thermocouple or thermistor, may be mounted on ablation surfaces on the distal portion of the catheter 14 as described below.

The console 24 typically contains one or more ablation power generators 25. The catheter 14 may be adapted to conduct ablative energy to the heart using any known ablation technique, e.g., radiofrequency energy, ultra-sound energy, irreversible electroporation and laser-produced light energy. Such methods are disclosed in U.S. Pat. Nos. 6,814,733, 6,997,924, and 7,156,816.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. Nos. 7,756,576, and 7,536,218.

As noted above, the catheter 14 is coupled to the console 24, which enables the operator 16 to observe and regulate the functions of the catheter 14. Console 24 includes the processor 22, generally a computer with appropriate signal processing circuits. The processor 22 is coupled to drive a display 29 (e.g., a monitor). The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the display 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site may be provided. The system 10 may receive image data from an external imaging modality, such as an MRI unit or the like and includes image processors that can be incorporated in or invoked by the processor 22 for generating and displaying images.

In practice, some or all of the functions of the processor 22 may be combined in a single physical component or, alternatively, implemented using multiple physical components. These physical components may comprise hard-wired or programmable devices, or a combination of the two. In some embodiments, at least some of the functions of the processor 22 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Figures 2, 3:
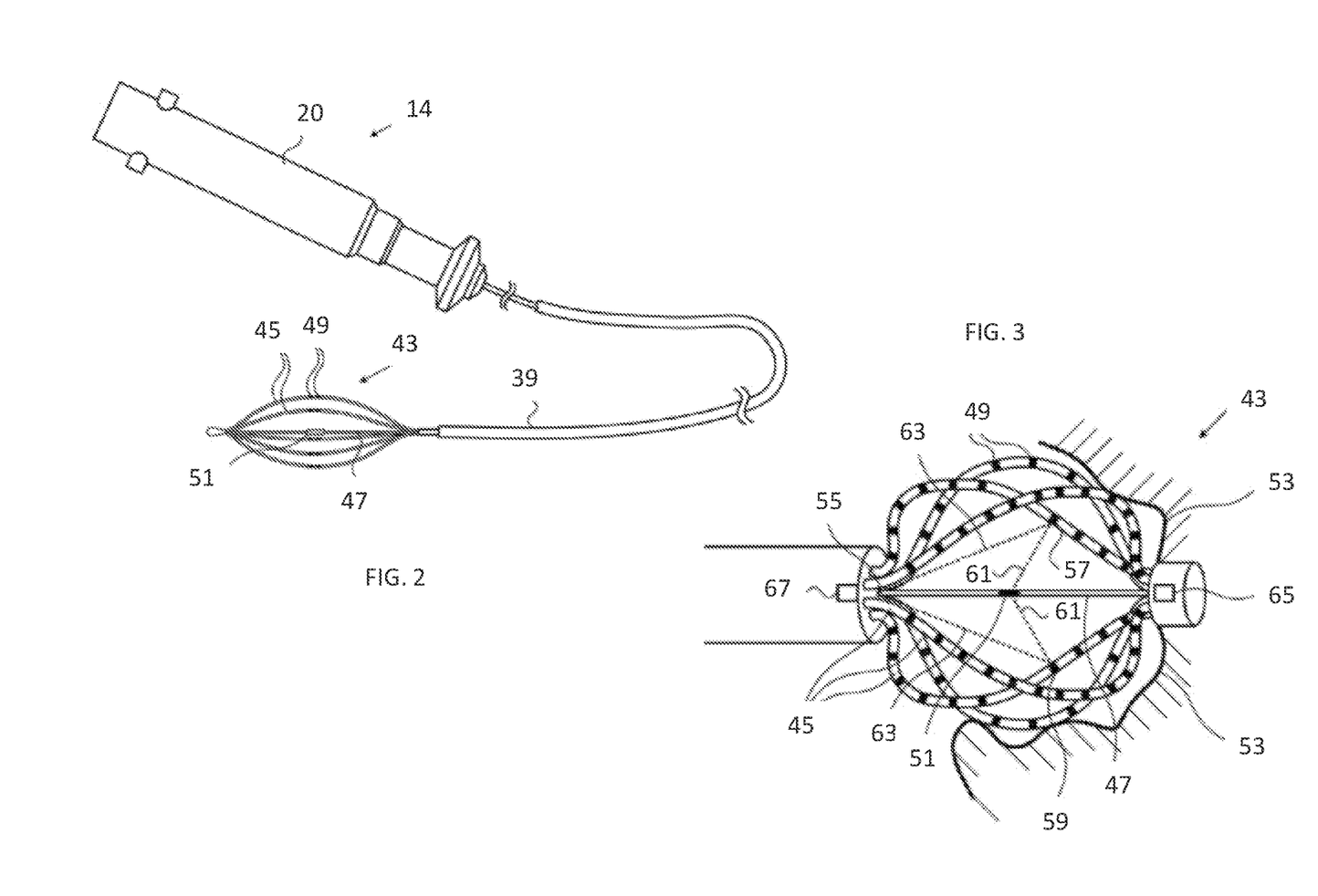
FIG. 2 is a perspective view of a catheter for use with the system of FIG. 1.
FIG. 3 is a detailed schematic view of an electrode assembly for use with the system of FIG. 1.

Reference is now made to FIG. 2, which is a perspective view of the catheter 14 for use with the system 10 of FIG. 1.

The catheter 14 comprises an elongated shaft 39 having proximal and distal ends, the control handle 20 at the proximal end of the catheter body, and an expandable distal end basket assembly 43 mounted at the distal end of the shaft 39.

The shaft 39 comprises an elongated tubular construction having a single, axial or central lumen (not shown), but can optionally have multiple lumens if desired. The shaft 39 is flexible, i.e., bendable, but substantially non-compressible along its length. The shaft 39 can be of any suitable construction and made of any suitable material. In some embodiments, the elongated shaft 39 comprises an outer wall made of polyurethane or polyether block amide. The outer wall comprises an imbedded braided mesh of stainless steel or the like to increase torsional stiffness of the shaft 39 so that, when the control handle 20 is rotated, the distal end of the shaft 39 rotates in a corresponding manner.

The outer diameter of the shaft 39 is not critical, but may be in the range of about 2 to 5 mm. Likewise, the thickness of the outer wall is not critical, but is generally thin enough so that the central lumen can accommodate any one or more of the following: a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905.

The assembly 43 is mounted to the distal end of the shaft 39. As shown in FIG. 2, the basket assembly 43 comprises five splines 45 or arms mounted, generally evenly-spaced, around a contraction wire 47, which is connected to the distal extremity of the assembly 43, and which contracts, retracts and expands the assembly 43 when a tractive or a pushing force is applied longitudinally to the contraction wire 47 as the case may be. The contraction wire 47 forms a longitudinal axis of symmetry for the assembly 43. The splines 45 are all attached, directly or indirectly, to the contraction wire 47 at their distal ends, and to the shaft 39 at their proximal ends. When the contraction wire 47 is moved longitudinally to expand and contract the assembly 43, in the expanded position the splines 45 are bowed outwardly and in the contracted position the splines 45 are generally straight. As will be recognized by one skilled in the art, the number of splines 45 can vary as desired depending on the particular application, so that the assembly 43 has at least two splines, generally at least three splines, and as many as ten or more splines. The expandable distal end basket assembly 43 is not limited to the depicted configuration, but can include other designs, such as spherical or egg-shaped designs, that include a plurality of expandable arms connected, directly or indirectly, at their proximal and distal ends.

The assembly 43 includes at least one sensing electrode 49 disposed thereon. In some embodiments, each of the splines 45 may comprise a flexible wire with a non-conductive covering on which one or more of the sensing electrodes 49 (e.g., ring spline electrodes) are mounted. The electrodes 49 are termed as "sensing electrodes" for the sake of convenience, but may also be used to perform ablation. In some embodiments, the flexible wires each comprise a flat nitinol wire and the non-conductive coverings each comprise a biocompatible plastic tubing, such as polyurethane or polyimide tubing. Alternatively, the splines 45 can be designed without the internal flexible wire if a sufficiently rigid nonconductive material is used for the non-conductive covering to permit expansion of the assembly 43, so long as the spline has an outer surface that is non-conductive over at least a part of its surface for mounting of the sensing electrodes 49. In some embodiments, the splines may be formed from flexible polymer strip circuits with electrodes 49 being disposed on an outer surface of each of the flexible polymer strip circuits.

Each of the sensing electrodes 49 on the splines 45 is electrically connected to an appropriate mapping or monitoring system and/or source of ablation energy by means of an electrode lead wire (not shown). The electrode lead wires extend through the control handle 20, through a lumen in the shaft 39, into the non-conductive covering of corresponding splines 45, and attach to their corresponding sensing electrodes 49 by any suitable method. The catheter 14 includes a far-field electrode 51, e.g., a cylindrical electrode, disposed on the contraction wire 47. The far-field electrode 51 is disposed in the expandable distal end basket assembly 43 to prevent the far-field electrode 51 from contacting the tissue of the cardiac chamber of the heart 12. In some embodiments, the catheter 14 may include more than one far-field electrode 51.

The function of the far-field electrode 51 is described below. In some embodiments, the far-field electrode 51 may be provided on a different catheter which is inserted into the heart 12 at the same time as the catheter 14. Additional details of the catheter 14 are described in the above-referenced U.S. Pat. No. 6,748,255.

The catheter 14 typically has multiple electrodes 49 arranged on multiple flexible splines of the basket assembly 43. The catheter 14 is configured to be inserted into a cardiac chamber of the heart 12 (FIG. 1) in a collapsed form, where the splines 45 are relatively close together. Once in the heart 12, the splines 45 may be formed into their expanded basket shape by the contraction wire 47, which holds distal ends of the splines 45, and pulls the distal ends of the splines 45 in a proximal direction.

Reference is now made to FIG. 3, which is a detailed schematic view of the expandable distal end basket assembly 43 of FIG. 2. In expanded form of the assembly 43 at least a portion of the sensing electrodes 49 of the splines 45 contact endocardial surface 53 of the heart 12 and acquire signals corresponding to electropotentials generated at their points of contact with the surface. However, since the sensing electrodes 49 are in a conductive medium (the blood), in addition to the electropotentials from the points of contact, the acquired signals also include far-field components from other regions of the heart 12.

The far-field components constitute an interfering signal on the endocardial surface electropotentials. To counteract the interference, embodiments of the present invention position the far-field electrode 51 on the contraction wire 47. In the expanded configuration of the assembly 43, the far-field electrode 51 is located on the contraction wire 47 so as to be approximately equidistant from all corresponding sensing electrodes 49, i.e., sensing electrodes 49 that are equidistant from a fixed reference point on the long axis of the catheter, such as reference point 55 at the proximal end of the assembly 43, and is prevented from contacting the surface of the heart by the splines 45. For example, electrodes 57, 59 are equidistant from reference point 55, and are also equidistant from the far-field electrode 51, as indicated by broken lines 61, 63, respectively. When the far-field electrode 51 is at least 0.5 cm removed from the sensing electrodes 49 in the expanded configuration of the assembly 43 it acquires a far-field signal, but not a near-field signal from the endocardial surface 53. However, the signals e(t) acquired by the sensing electrodes 49 have both a far-field and a surface (near-field) component. The far-field component signal x(t) acquired by the far-field electrode 51 is removed from the signals e(t) acquired by the sensing electrodes 49 so as to counteract the interference suffered by these electrodes, i.e., by subtraction of the signals: e(t)−x(t). Additionally, or alternatively, removal of the far-field component may be accomplished using any suitable method.

In some embodiments, the catheter 14 is provided with a distal location sensor 65 mounted at or near the position where the distal ends of the spines are connected, and a proximal location sensor 67 mounted at or near the proximal end of the assembly 43, whereby, in use, the co-ordinates of the location sensor 65 relative to those of the location sensor 67 can be determined and taken together with known information pertaining to the curvature of the splines 45 to find the positions of each of the sensing electrodes 49.

Figure 4:
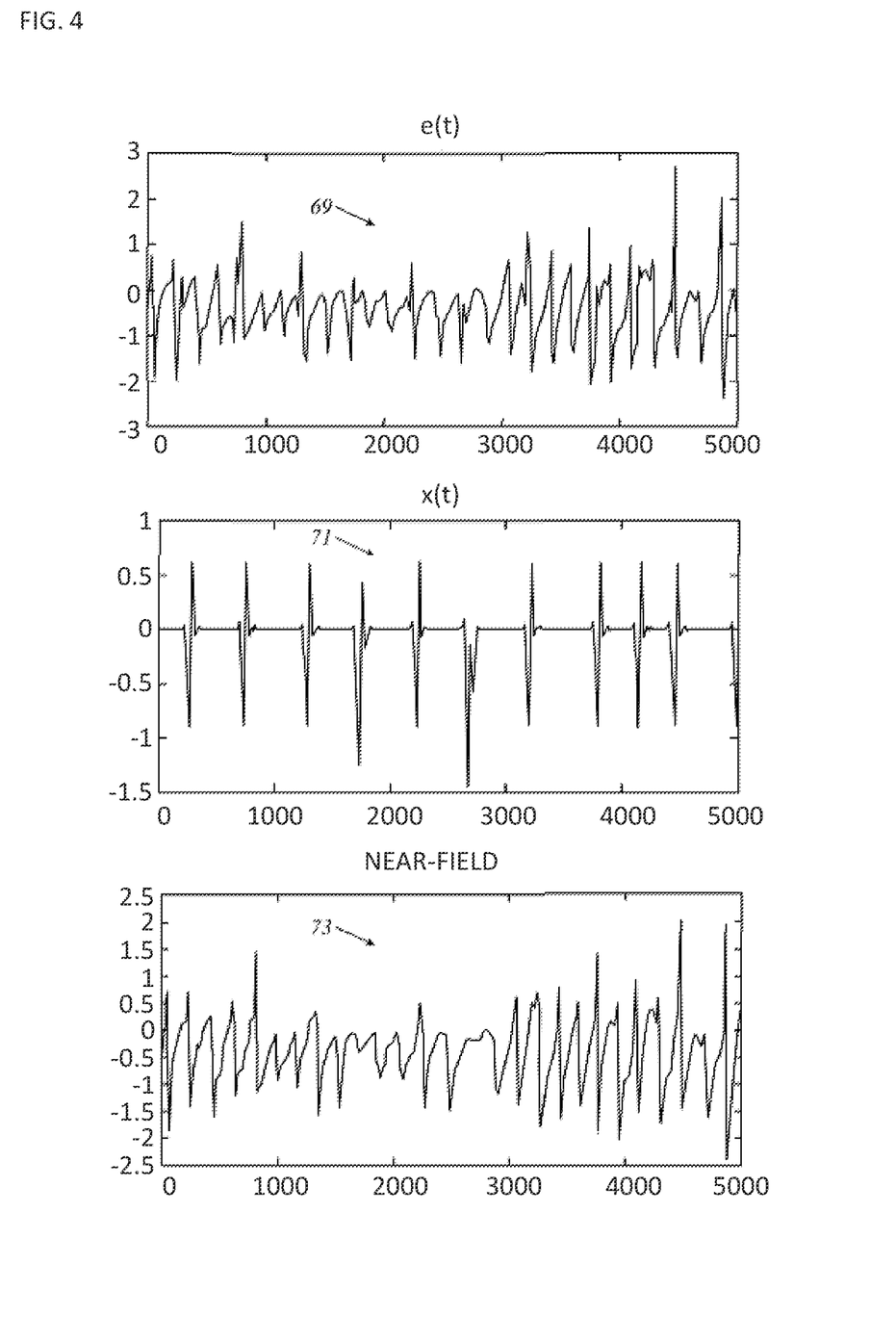
FIG. 4 is a prospective graph of signals that may be obtained using the electrode assembly of FIG. 3.

Reference is now made to FIG. 4, which is a prospective graph of example signals that may be obtained using the assembly 43 of FIG. 3. A graph 69 shows an intracardiac signal e(t) obtained from a unipolar or bipolar configuration of the sensing electrodes 49. A graph 71 is a signal tracing x(t) of the far-field electrode 51, which may be a concurrent tracing. A graph 73 is a tracing of the signal obtained when the far-field component in the electrogram e(t) is removed by subtraction of the signal of graph 71 from the signal of graph 69 or by application, mutatis mutandis, of the algorithms described in US Patent Publication No. 2016/0175023, or U.S. Pat. No. 9,554,718.

Figure 5:
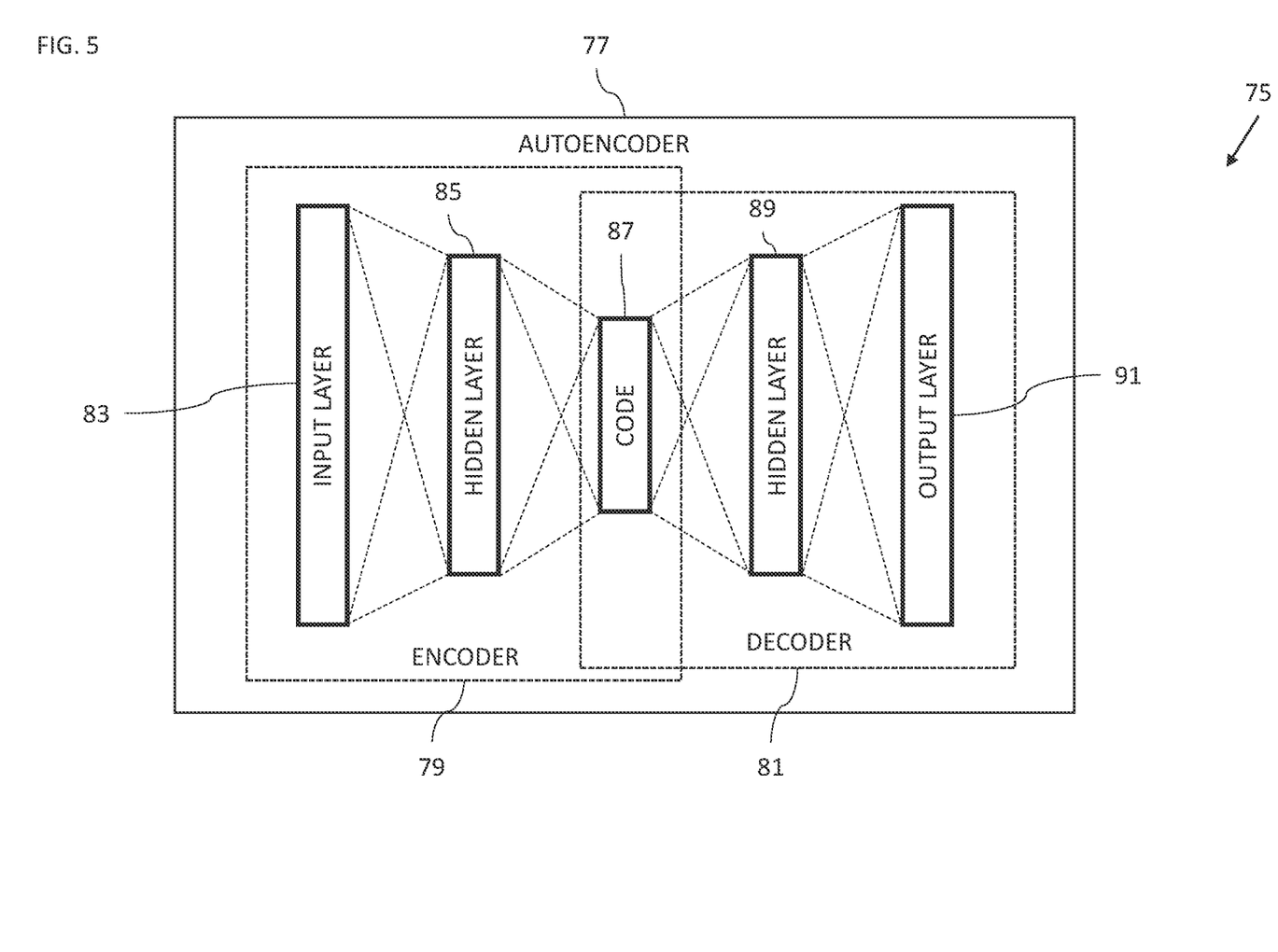
FIG. 5 is a schematic view of an artificial neural network for use with the system of FIG. 1.

Reference is now made to FIG. 5, which is a schematic view of an artificial neural network 75 for use with the system 10 of FIG. 1.

A neural network is a network or circuit of neurons, or in a modern sense, an artificial neural network, composed of artificial neurons or nodes. The connections of the biological neuron are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1.

These artificial networks may be used for predictive modeling, adaptive control and applications and can be trained via a dataset. Self-learning resulting from experience can occur within networks, which can derive conclusions from a complex and seemingly unrelated set of information.

For completeness, a biological neural network is composed of a group or groups of chemically connected or functionally associated neurons. A single neuron may be connected to many other neurons and the total number of neurons and connections in a network may be extensive. Connections, called synapses, are usually formed from axons to dendrites, though dendrodendritic synapses and other connections are possible. Apart from the electrical signaling, there are other forms of signaling that arise from neurotransmitter diffusion.

Artificial intelligence, cognitive modeling, and neural networks are information processing paradigms inspired by the way biological neural systems process data. Artificial intelligence and cognitive modeling try to simulate some properties of biological neural networks. In the artificial intelligence field, artificial neural networks have been applied successfully to speech recognition, image analysis and adaptive control, in order to construct software agents (in computer and video games) or autonomous robots.

A neural network (NN), in the case of artificial neurons called artificial neural network (ANN) or simulated neural network (SNN), is an interconnected group of natural or artificial neurons that uses a mathematical or computational model for information processing based on a connectionistic approach to computation. In most cases an ANN is an adaptive system that changes its structure based on external or internal information that flows through the network. In more practical terms, neural networks are non-linear statistical data modeling or decision-making tools. They can be used to model complex relationships between inputs and outputs or to find patterns in data.

In some embodiments, as shown in FIG. 5, the artificial neural network 75 may include an autoencoder 77 including an encoder 79 and a decoder 81. In other embodiments, the artificial neural network 75 may comprise any suitable ANN. The artificial neural network 75 may be implemented in software and/or hardware.

The encoder 79 includes an input layer 83 into which an input is received. The encoder then includes one or more hidden layers 85 which progressively compress the input to a code 87. The decoder 81 includes one or more hidden layers 89 which progressively decompress the code 87 up to an output layer 91 from which the output of the autoencoder 77 is provided. The autoencoder 77 includes weights between the layers of the autoencoder 77. The autoencoder 77 manipulates the data received at the input layer 83 according to the values of the various weights between the layers of the autoencoder 77.

The weights of the autoencoder 77 are updated during training of the autoencoder 77 so that the autoencoder 77 performs a data manipulation task that the autoencoder 77 is trained to perform. In the example of FIG. 5, the autoencoder 77 is trained to remove far-field components from intracardiac signals as described in more detail with reference to FIGS. 6 and 7.

The number of layers in the autoencoder 77 and the width of the layers may be configurable. As the number of layers and width of the layers increases so does the accuracy to which the autoencoder 77 can manipulate data according to the task at hand. However, a larger number of layers, and wider layers, generally requires more training data, more training time and the training may not converge. By way of example, the input layer 83 may include 400 neurons (e.g., to compress a batch of 400 samples). The encoder 79 may include five layers which compress by a factor of two (e.g., 400, 200, 100, 50, 25). The decoder may include five layers which decompress by a factor of 2 (e.g., 25, 50, 100, 200, 400).

Figure 6:
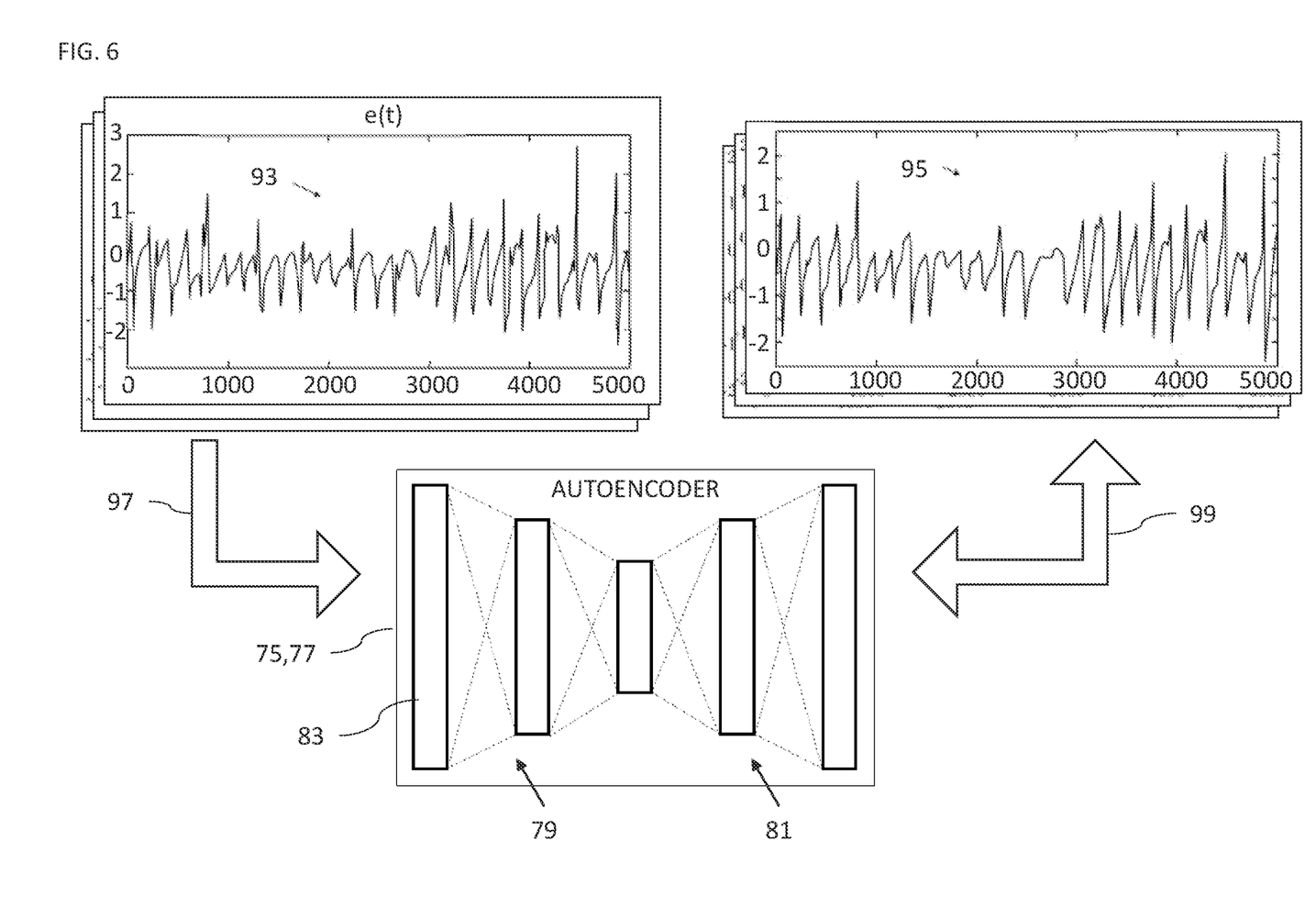
FIG. 6 is a schematic view illustrating training of the artificial neural network of FIG. 5.
Figure 7:
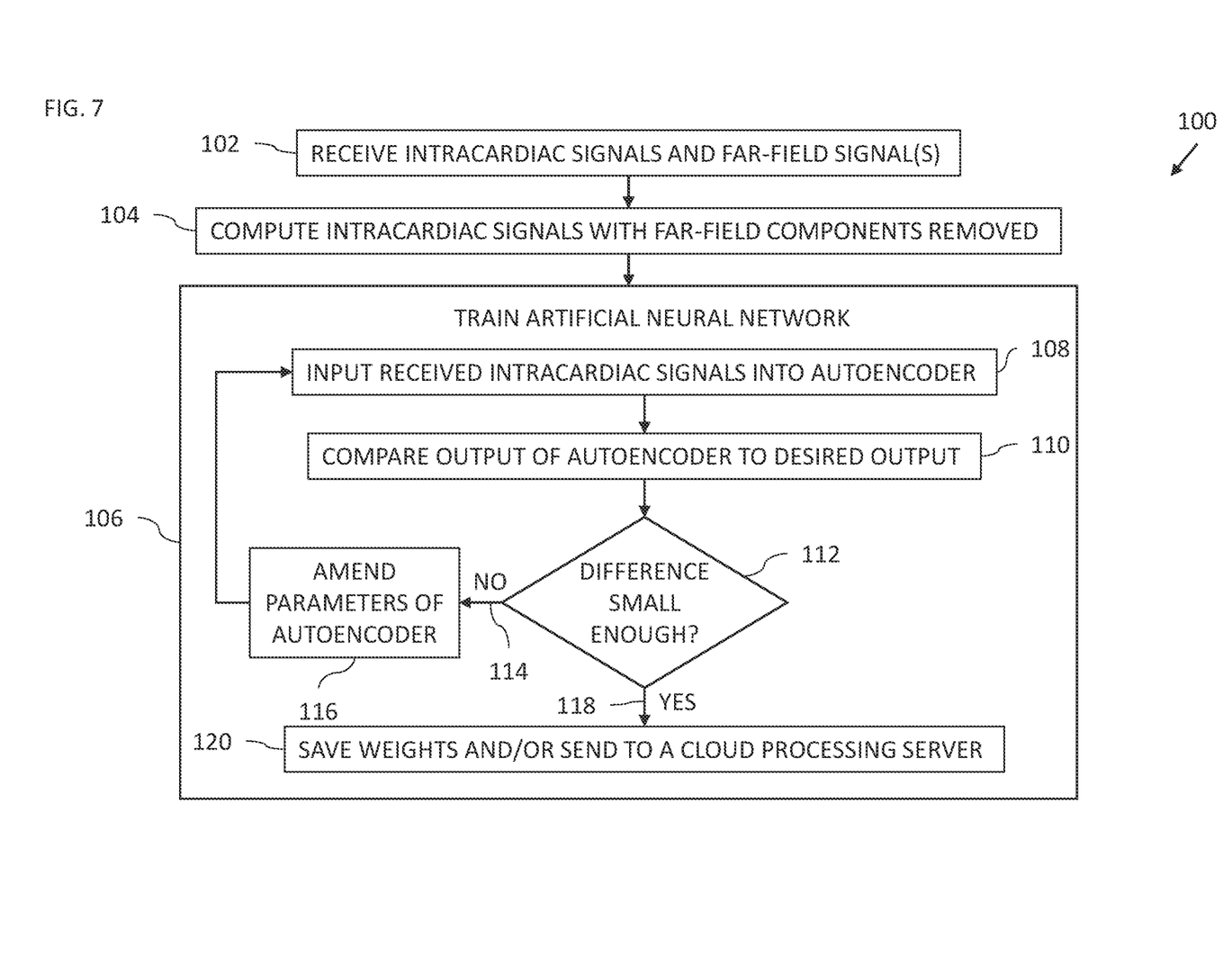
FIG. 7 is a flowchart including steps in a method to train the artificial neural network of FIG. 5.

Reference is now made to FIGS. 6 and 7. FIG. 6 is a schematic view illustrating training of the artificial neural network 75 of FIG. 5. FIG. 7 is a flowchart 100 including steps in a method to train the artificial neural network 75 of FIG. 5.

The artificial neural network 75 is trained based on data captured from a catheter such as the catheter 14 of FIGS. 1-3. The electrodes 49 (FIG. 3) of the catheter 14 are in contact with the tissue (e.g., endocardial surface 53 (FIG. 3) of the chamber of the heart 12 (FIG. 1). The electrodes 49 provide intracardiac signals 93 which include far-field components. In order to provide high quality training data, the operator 16 generally confirms that there is a good quality of contact between the electrodes 49 providing the intracardiac signals 93 and the tissue. The far-field electrode(s) 51 (FIG. 3) of the catheter 14 provides at least one far-field signal.

The processor 22 (FIG. 1) is configured to receive (block 102) the intracardiac signals 93 comprising far-field components captured by one or more of the electrodes 49 in contact with tissue of the cardiac chamber of a living subject. The catheter 14 may provide signals 93 from different electrodes 49 while in a given position within the cardiac chamber and/or from one or more electrodes 49 while the catheter 14 is moved to different positions in the cardiac chamber. The intracardiac signals 93 may be provided from different cardiac chambers and even from different living subjects.

The processor 22 (FIG. 1) is also configured to receive (block 102) the far-field signal(s) captured by the far-field electrode 51 (inserted into the cardiac chamber and not in contact with the tissue of the cardiac chamber) concurrently with the intracardiac signals 93 captured by the electrode(s) 49 of the catheter 14 in whatever positions the catheter 14 is moved while the intracardiac signals 93 are captured. Therefore, each of the intracardiac signals 93 has a corresponding far-field signal captured over the same time interval that the intracardiac signal 93 was captured. Multiple intracardiac signals 93 may have the same corresponding far-field signal captured at the same time as the multiple intracardiac signals 93.

In some embodiments, the processor 22 (FIG. 1) is configured to compute (block 104) the intracardiac signals 93 with the respective far-field components removed responsively to the far-field signal(s), yielding cleaned intracardiac signals 95. The cleaned intracardiac signals 95 may be computed using one of the methods described above with reference to FIG. 3 or any suitable method for removing far-field components from intracardiac signals.

The processor 22 is configured to train (block 106) the artificial neural network 75 (e.g., the autoencoder 77) to remove far-field components from intracardiac signals responsively to the received intracardiac signals 93 and the far-field signal(s) captured by the far-field electrode 51. In some embodiments, the processor 22 is configured to train the artificial neural network 75 responsively to the intracardiac signals 93 and the computed cleaned intracardiac signals 95 (i.e., the intracardiac signals 93 with the respective far-field components removed).

Training the artificial neural network 75 is generally an iterative process. One method of training the artificial neural network 75 is now described below.

The processor 22 is configured to input (block 108, arrow 97) the received intracardiac signals 93 into the artificial neural network 75. For example, the intracardiac signals 93 are input into the input layer 83 of the encoder 79. The processor 22 is configured to compare (block 110, arrow 99) the output of the artificial neural network 75 (e.g., the output of the decoder 81 of the autoencoder 77) with the desired output, i.e., the corresponding cleaned intracardiac signals 95. For example, if there is a set of intracardiac signals A, B, C output by the artificial neural network 75 and a corresponding set of cleaned intracardiac signals A', B', and C', the processor 22 compares A with A', B with B', C with C' and so on. The comparison is generally performed using a suitable loss function, which computes the overall difference between all the outputs of the artificial neural network 75 and all the desired outputs (e.g., all the corresponding cleaned intracardiac signals 95).

At a decision block 112, the processor 22 is configured to determine if the difference between the output of the artificial neural network 75 and desired output is small enough. If the difference between the output of the artificial neural network 75 and the desired output is small enough (branch 118), the processor 22 is configured to save (block 120) the parameters (e.g., weights) of the artificial neural network 75 (e.g., the autoencoder 77) and/or send the parameters (e.g., weights) to a cloud processing server (not shown).

If the difference is not small enough (branch 114), the processor 22 is configured to amend (block 116) parameters (e.g., weights) of the artificial neural network 75 (e.g., of the autoencoder 77) to reduce the difference between the output of the artificial neural network 75 and the desired output of the artificial neural network 75. The difference being minimized in the above example is the overall difference between all the outputs of the artificial neural network 75 and all the desired outputs (e.g., all the corresponding cleaned intracardiac signals 95). The processor 22 is configured to amend the parameters using any suitable optimization algorithm, for example, a gradient descent algorithm such as Adam Optimization. The steps of blocks 108, 110, and 112 are then repeated.

Figure 8:
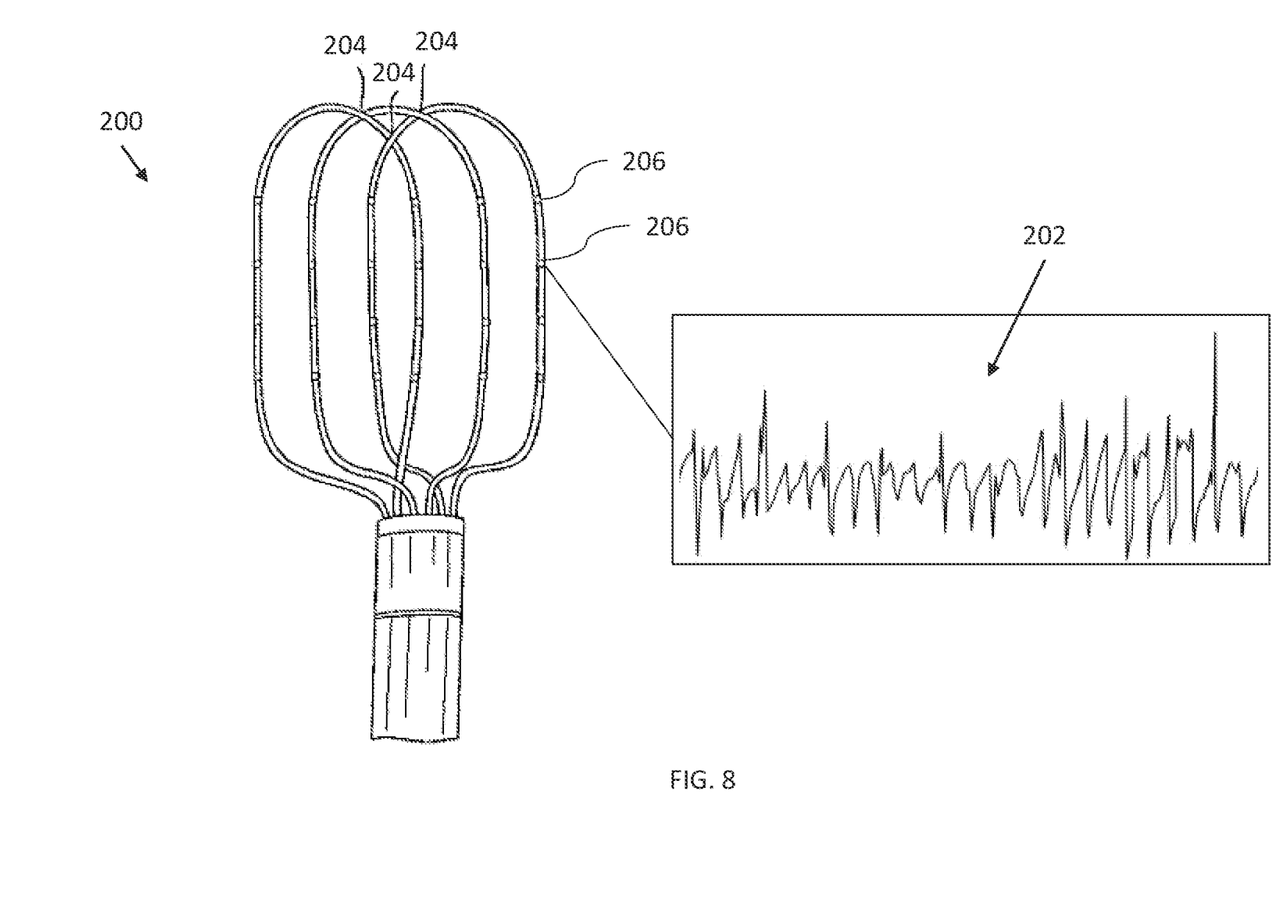
FIG. 8 is a schematic view of a catheter and a signal captured by the catheter for use in the system of FIG. 1.

Reference is now made to FIG. 8, which is a schematic view of a catheter 200 and an intracardiac signal 202 captured by the catheter 200 for use in the system 10 of FIG. 1. The catheter 200 is a flat grid catheter including multiple splines 204 with electrodes 206 (only some labeled for the sake of simplicity) on each spline 204. The catheter 200 is configured to be inserted into a cardiac chamber of a living subject. The living subject may be: the same living subject into which the catheter 14 was inserted and according to which the artificial neural network 75 was trained; or a different living subject.

The catheter 200 does not include an electrode which does not generally come into contact with cardiac tissue and therefore capturing a signal which is representative of the far-field alone would be very difficult to achieve with the catheter 200. The medical system 10 is configured to remove the far-field component from the intracardiac signal 202 using the trained artificial neural network 75 (FIG. 6) as described in more detail with reference to FIGS. 9 and 10 below.

The catheter 200 is an example of a catheter which provides an intracardiac signal including a far-field component to be removed. Any suitable catheter (e.g., a balloon catheter) or even one including a far-field electrode (e.g., a suitable basket catheter), may provide an intracardiac signal which is then processed using the trained artificial neural network 75 to remove the far-field component from the provided intracardiac signal.

Figure 9:
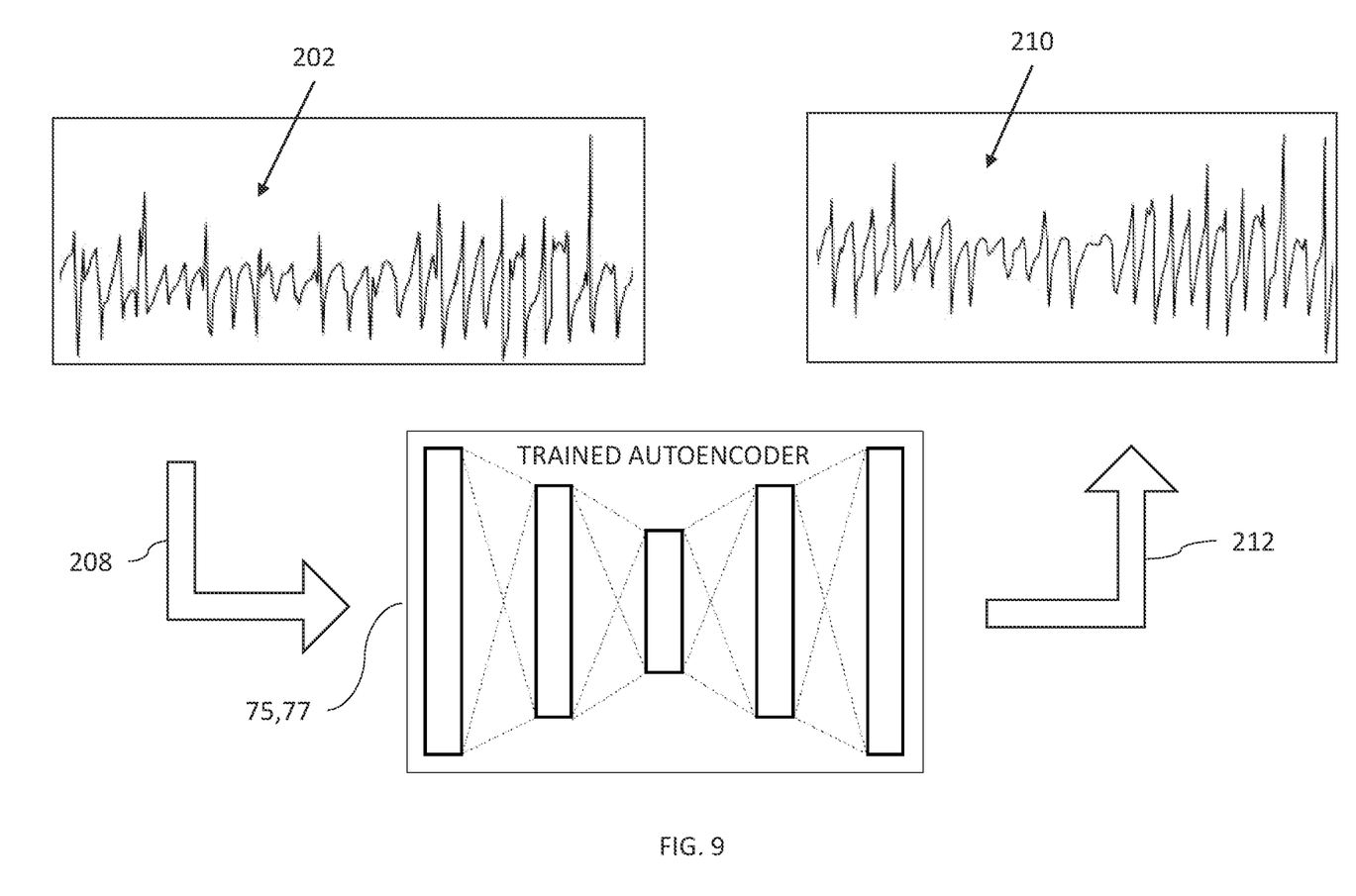
FIG. 9 is a schematic view illustrating processing of the captured signal of FIG. 8 being processed by the trained artificial neural network.
Figure 10:
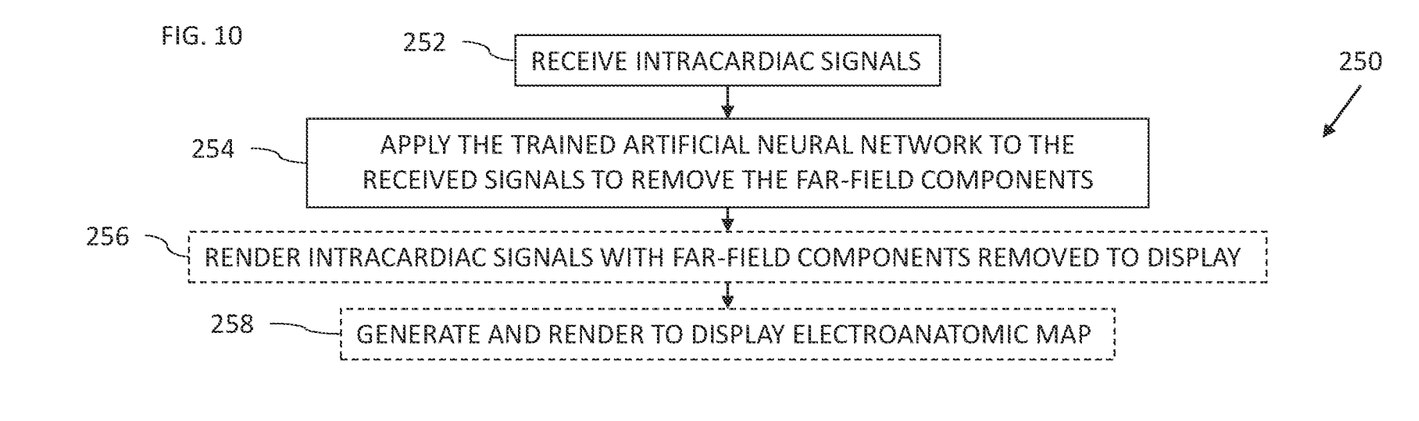
FIG. 10 is a flowchart including steps in a method to process the captured signal of FIG. 8 using the trained artificial neural network.

Reference is now made to FIGS. 9 and 10. FIG. 9 is a schematic view illustrating processing of the captured signal 202 of FIG. 8 being processed by the trained artificial neural network 75. FIG. 10 is a flowchart 250 including steps in a method to process the captured signal 202 of FIG. 8 using the trained artificial neural network 75. Reference is also made to FIG. 8.

The processor 22 (FIG. 1) is configured to receive (block 252) intracardiac signal(s) 202 captured by the sensing electrode(s) 206 of the catheter 200 inserted into a cardiac chamber of a living subject. The processor 22 is configured to apply (block 254, arrow 208) the trained artificial neural network 75 to the intracardiac signal(s) 202 to remove respective far-field component(s) from the intracardiac signal(s) 202 yielding (arrow 212) respective cleaned intracardiac signal(s) 210.

In some embodiments, the trained artificial neural network comprises the trained autoencoder 77. In these embodiments, the processor 22 (FIG. 1) is configured to apply the autoencoder 77 to the intracardiac signal(s) 202 to remove the respective far-field components from the intracardiac signal(s) 202.

Figure 11:
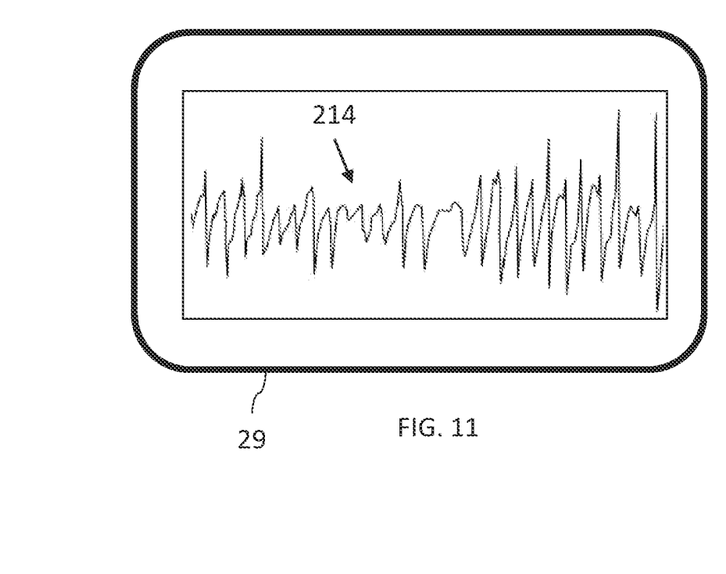
FIG. 11 is a schematic view of a displayed intracardiac signal.

Reference is now made to FIG. 11, which is a schematic view of a displayed intracardiac signal representation 214. Reference is also made to FIG. 10. The processor 22 (FIG. 1) is optionally configured to render (block 256) to the display 29 representation 214 of the cleaned intracardiac signal(s) 210 (FIG. 9) (i.e., the intracardiac signal(s) 202 with respective far-field component(s) removed).

Figure 12:
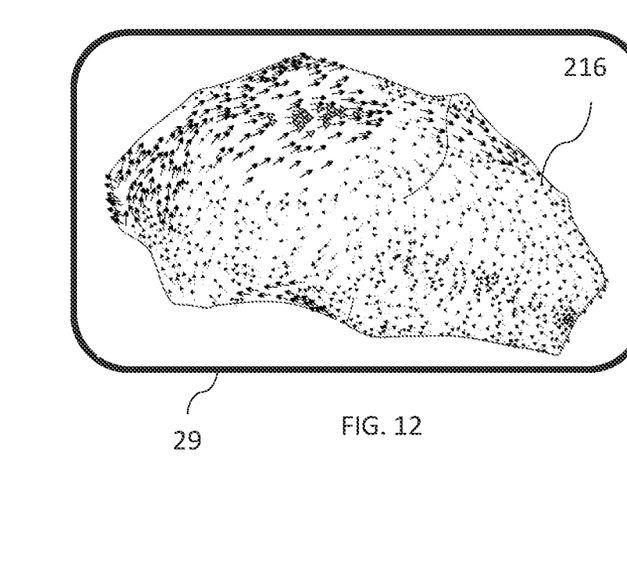
FIG. 12 is a schematic view of a displayed electroanatomic map.

Reference is now made to FIG. 12, which is a schematic view of a displayed electroanatomic map 216. Reference is also made to FIG. 10. The processor 22 (FIG. 1) is optionally configured to generate and render (block 258) to the display 29, the electroanatomic map 216 responsively to the cleaned intracardiac signal(s) 210 (i.e., the intracardiac signal(s) 202 with respective far-field component(s) removed).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A method for analyzing signals, comprising:
   receiving: first intracardiac signals comprising first far-field components captured by at least one first sensing electrode of a first catheter, the at least one sensing electrode being in contact with tissue of a cardiac chamber of a first living subject; and at least one far-field signal captured from at least one far-field electrode inserted into the cardiac chamber and not in contact with the tissue of the cardiac chamber;
   training an artificial neural network to remove far-field components from intracardiac signals responsively to the received first intracardiac signals and the at least one far-field signal;
   receiving second intracardiac signals captured by at least one second sensing electrode of a second catheter inserted into a cardiac chamber of a second living subject; and
   applying the trained artificial neural network to the second intracardiac signals to remove respective second far-field components from the second intracardiac signals.

2. The method according to claim 1, further comprising computing the first intracardiac signals with the respective first far-field components removed responsively to the at least one far-field signal, wherein the training includes training the artificial neural network responsively to the computed first intracardiac signals with the respective first far-field components removed.

3. The method according to claim 1, wherein the training comprises training an autoencoder comprising an encoder and a decoder.

4. The method according to claim 1, further comprising rendering to a display a representation of at least one of the second intracardiac signals with a respective one of the second far-field components removed.

5. The method according to claim 1, further comprising generating and rendering to a display, an electroanatomic map responsively to at least one of the second intracardiac signals with a respective one of the second far-field components removed.

6. The method according to claim 1, wherein the first catheter includes the at least one far-field electrode.

7. A software product, comprising a non-transient computer-readable medium in which program instructions are stored, which instructions, when read by a central processing unit (CPU), cause the CPU to:
   receive: first intracardiac signals comprising first far-field components captured by at least one first sensing electrode of a first catheter, the at least one sensing electrode being in contact with tissue of a cardiac chamber of a first living subject; and at least one far-field signal captured from at least one far-field electrode inserted into the cardiac chamber and not in contact with the tissue of the cardiac chamber;
   train an artificial neural network to remove far-field components from intracardiac signals responsively to the received first intracardiac signals and the at least one far-field signal
   receive second intracardiac signals captured by at least one second sensing electrode of a second catheter inserted into a cardiac chamber of a second living subject; and
   apply the trained artificial neural network to the second intracardiac signals to remove respective second far-field components from the second intracardiac signals.

8. The software product according to claim 7, wherein the instructions, when read by the CPU, also cause the CPU to:
   compute the first intracardiac signals with the respective first far-field components removed responsively to the at least one far-field signal; and
   train the artificial neural network responsively to the computed first intracardiac signals with the respective first far-field components removed.

9. The software product according to claim 7, wherein the instructions, when read by the CPU, also cause the CPU to render to a display a representation of at least one of the second intracardiac signals with a respective one of the second far-field components removed.

10. The software product according to claim 7, wherein the instructions, when read by the CPU, also cause the CPU to generate and render to a display, an electroanatomic map responsively to at least one of the second intracardiac signals with a respective one of the second far-field components removed.

11. A medical system, comprising:
   a first catheter including at least one first sensing electrode configured to be inserted into a cardiac chamber of a first living subject; and
   a second catheter comprising at least one second sensing electrode configured to be inserted into a cardiac chamber of a second living subject;
   a processor configured to:
      receive: first intracardiac signals comprising first far-field components captured by the at least one first sensing electrode of the first catheter, the at least one sensing electrode being in contact with tissue of the cardiac chamber of the first living subject; and at least one far-field signal captured from the at least one far-field electrode inserted into the cardiac chamber and not in contact with the tissue of the cardiac chamber;

train an artificial neural network to remove far-field components from intracardiac signals responsively to the received first intracardiac signals and the at least one far-field signal;

receive second intracardiac signals captured by the at least one second sensing electrode of the second catheter inserted into the cardiac chamber of the second living subject; and apply the trained artificial neural network to the second intracardiac signals to remove respective second far-field components from the second intracardiac signals.

12. The system according to claim 11, wherein the processor is configured to:

compute the first intracardiac signals with the respective first far-field components removed responsively to the at least one far-field signal; and train the artificial neural network responsively to the computed first intracardiac signals with the respective first far-field components removed.

13. The system according to claim 11, wherein the artificial neural network comprises an autoencoder including an encoder and a decoder, the processor being configured to train the autoencoder to remove the far-field components from intracardiac signals responsively to the received first intracardiac signals and the at least one far-field signal.

14. The system according to claim 11, wherein the trained artificial neural network comprises an autoencoder including an encoder and a decoder, the processor being configured to apply the autoencoder to the second intracardiac signals to remove the respective second far-field components from the second intracardiac signals.

15. The system according to claim 11, further comprising a display, wherein the processor is configured to render to the display a representation of at least one of the second intracardiac signals with a respective one of the second far-field components removed.

16. The system according to claim 11, further comprising a display, wherein the processor is configured to generate and render to the display, an electroanatomic map responsively to at least one of the second intracardiac signals with a respective one of the second far-field components removed.

17. The system according to claim 11, wherein the first catheter includes the at least one far-field electrode.

18. The system according to claim 17, wherein the first catheter comprises an expandable distal end basket assembly, the at least one first sensing electrode being disposed on the basket assembly, the at least one far-field electrode being disposed in the basket assembly to prevent the at least one far-field electrode from contacting the tissue of the cardiac chamber of the first living subject.

* * * * *